(12) United States Patent
Jepson et al.

(10) Patent No.: US 11,317,832 B2
(45) Date of Patent: May 3, 2022

(54) SENSOR DATA MANAGEMENT FOR MULTIPLE SMART DEVICES

(71) Applicant: Intel Corporation, Santa Clara, CA (US)

(72) Inventors: Daniel Jepson, San Jose, CA (US); Charles Carter Jernigan, Santa Clara, CA (US); Nicholas Moe Khosravy, Palo Alto, CA (US); John Wei, Saratoga, CA (US); Fai Yeung, Palo Alto, CA (US)

(73) Assignee: Intel Corporation, Santa Clara, CA (US)

( * ) Notice: Subject to any disclaimer, the term of this patent is extended or adjusted under 35 U.S.C. 154(b) by 1614 days.

(21) Appl. No.: 15/089,411

(22) Filed: Apr. 1, 2016

(65) Prior Publication Data

US 2017/0289738 A1 Oct. 5, 2017

(51) Int. Cl.
*A61B 5/11* (2006.01)
*H04W 4/80* (2018.01)
*A61B 5/00* (2006.01)

(52) U.S. Cl.
CPC .......... *A61B 5/1118* (2013.01); *A61B 5/0024* (2013.01); *A61B 5/684* (2013.01); *A61B 5/6898* (2013.01); *A61B 5/7221* (2013.01); *H04W 4/80* (2018.02)

(58) Field of Classification Search
None
See application file for complete search history.

(56) References Cited

U.S. PATENT DOCUMENTS

| | | | |
|---|---|---|---|
| 2006/0282021 A1* | 12/2006 | DeVaul | A61B 5/1117 600/595 |
| 2012/0167170 A1* | 6/2012 | Shi | G06F 21/32 726/2 |
| 2012/0245855 A1* | 9/2012 | Kamath | A61B 5/01 702/19 |
| 2015/0156031 A1* | 6/2015 | Fadell | G08B 19/005 700/276 |

(Continued)

FOREIGN PATENT DOCUMENTS

WO 2017172250 A1 10/2017

OTHER PUBLICATIONS

International Search Report and Written Opinion in International Patent Application No. PCT/US2017/020537 dated May 24, 2017, 10 pages.

*Primary Examiner* — Kyle R Quigley
*Assistant Examiner* — Denise R Karavias
(74) *Attorney, Agent, or Firm* — Patent Capital Group (57) ABSTRACT

One embodiment relates to an apparatus, comprising logic, at least partially incorporated into hardware, to: receive first sensor data associated with a first sensor of a first smart device; determine a first reliability factor associated with the first sensor data; receive second sensor data associated with a second sensor of a second smart device; and determine a second reliability factor associated with the second sensor data. The logic is further to determine a sensor data reporting plan based upon the first reliability factor and the second reliability factor, the sensor data reporting plan indicating whether each of the first sensor and the second sensor are to subsequently send their respective sensor data to a primary communication device.

22 Claims, 5 Drawing Sheets

(56) References Cited

U.S. PATENT DOCUMENTS

| | | | |
|---|---|---|---|
| 2015/0264028 A1* | 9/2015 | Kim | H04L 43/08 |
| | | | 726/3 |
| 2015/0373007 A1* | 12/2015 | Sheller | H04L 67/24 |
| | | | 726/6 |
| 2016/0234206 A1* | 8/2016 | Tunnell | H04W 4/70 |
| 2019/0007517 A1* | 1/2019 | Jagannath | G01D 5/00 |

* cited by examiner

SENSOR DATA MANAGEMENT FOR MULTIPLE SMART DEVICES

TECHNICAL FIELD

This application relates to the field of computing, and more particularly to sensor data management for multiple smart devices.

BACKGROUND

Bluetooth low energy (BLE) protocol is a wireless technology is a wireless communication protocol designed to allow wireless devices to communicate with one another within a wireless personal area network. Typical applications of the BLE protocol include health condition monitoring and fitness monitoring in which a smart device measures one or more parameters and reports the measurements to a primary communication device, such as a smartphone. ANT+ is another wireless protocol that is used to wirelessly transmit sensor data between a smart device, such as a heart rate monitor, a smartphone. Smart devices are generally electronic devices having the capability to connect, such as via a wirelessly connection, to other devices and/or networks and communicate at least somewhat autonomously via one or more protocols such as Bluetooth, WiFi, 4G, 3G, near field communication (NFC), ultrasound, etc. With the proliferation of different types of smart devices in which each may have different respective sets of sensors and sensor with respective accuracies and sensitivities to individual instantaneous conditions, collecting and maintaining the meaningfulness of all collected data from the sensors, which may or may not be consistent across different devices has become challenging. Moreover, running, for example, two different heart rate monitors on separate smart devices can be wasteful due to unnecessary, redundant, or inconsistent data being reported by the separate smart devices.

BRIEF DESCRIPTION OF THE DRAWINGS

Embodiments are illustrated by way of example and not limitation in the figures of the accompanying drawings, in which like references indicate similar elements and in which.

DETAILED DESCRIPTION OF EXAMPLE EMBODIMENTS

One or more example embodiments are directed to determining a sensor data reporting plan for a set of smart devices that is intelligent for the user, a given set of smart devices and their associated sensors, and the current circumstances applicable to the set of smart devices. In one or more embodiments, if two or more smart devices have associated sensors that collect the same or similar data, a primary communication device or one of the smart devices is configured to determine which of the sensors from the respective smart devices is the most appropriate to use at the current time based on a number of reliability factors such as sensor accuracy, usage context of the particular smart device, connectivity of the smart device, available battery life, remaining memory of the smart device, operating temperature of the smart device, pressure, etc. In one or more embodiments, the primary communication device or another smart device may instruct the smart device to disable a particular sensor of the smart device when it is determined that data from that particular sensor is not being used at the current time. In another embodiment, the primary communication device itself contains sensors and decisions may be made to use the primary communication device's sensors versus a smart device's sensors. For example, the primary communication device may contain a step counter and the user may have a BLE foot pod. Both collect step count information, and the primary communication device may decide which step count to use based on a variety of requirements such as power usage or accuracy.

Figure 1:
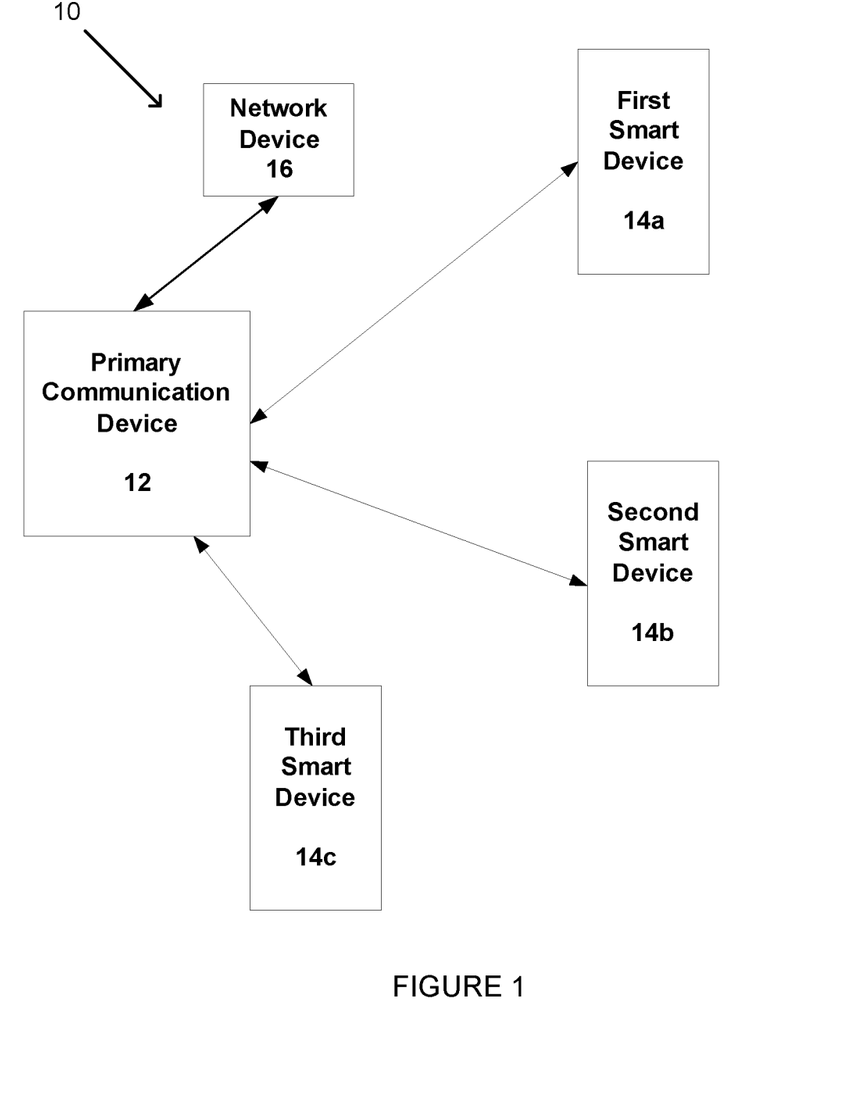
FIG. 1 illustrates an embodiment of a communication system for sensor data management for multiple smart devices.

FIG. 1 illustrates an embodiment of a communication system 10 for sensor data management for multiple smart devices. In the particular embodiment illustrated in FIG. 1, communication system 10 includes a primary communication device 12, a first smart device 14a, a second smart device 14b, a third smart device 14c, and a network device 16. Primary communication device 12 is configured to wirelessly communicate with each of first smart device 14a, second smart device 14b, and third smart device 14c to receive data measured or otherwise obtained by one or more sensors of each of the respective smart devices 14a-14c. In particular embodiments, primary communication device 12 communicates with each of first smart device 14a, second smart device 14b, and third smart device 14c using a Bluetooth low energy (BLE) communication protocol such as described in the Bluetooth Core Specification Version 4.0. In particular embodiments, primary communication device 12 is a communication and/or computing device, such as a smartphone, configured to receive sensor data obtained by one or more of first smart device 14a, second smart device 14b, and third smart device 14c. In particular embodiments, primary communication device 12 may be further configured to process the received data and perform one or more actions upon the processed data such as sending the processed data to a software application resident on primary communication device 12, displaying the processed data to a user of the primary communication device 12, and/or transmitting the processed data to a server. In accordance with various embodiments, network device 16 may include a server configured to exchange data, such as sensor data, with primary communication device 12. In still other particular embodiments, primary communications device 12 can include a tablet computer, a laptop computer, a desktop computer, a smart watch, or any other suitable communication device.

One or more of first smart device 14a, second smart device 14b, and third smart device 14c include a wireless device configured to measure, sense, or otherwise obtain sensor data, such as measurement values associated with biometric data, health data and/or fitness data, and communicate the data to primary communication device 12. In particular embodiments, first smart device 14a, second smart device 14*b*, and third smart device 14*c* may include one or more of a smart watch, a fitness and/or activity tracker, a health monitor, a navigation device, a media playback device, a smart phone, smart jewelry, smart glasses, a head-mounted optical display, a headset, an ear-bud or any other suitable electronic device configured to communicate data with primary communication device 12. In at least one embodiment, primary communication device 12 is configured to communicate with each of first smart device 14*a*, second smart device 14*b*, and third smart device 14*c* using a BLE protocol. In another embodiment, some of the smart devices are configured to communicate with primary communication device 12 via ANT+. In still other embodiments, first smart device 14*a*, second smart device 14*b*, and third smart device 14*c* are further configured to wirelessly communicate with one another using a wireless communication protocol such as BLE. Although the embodiment of FIG. 1 is illustrated using three smart devices in communication system 10, it should be understood that in other embodiments any number of smart devices may be present.

Conventional systems simply collect data sensor data from all smart devices to which a primary communication device, such as a smartphone, is connected. Each smart device is in effect treated independently as a source of information about or for the user. The primary communication device may also be another independent source of sensor data that is also collected. However, there are many situations in which the inelegance of this solution is problematic, especially when multiple smart devices and the primary communication device share the same or similar functionality, with the same or different reporting periods, and with the same or different sensitivities and statistical variations, according to different operating conditions, such as battery life available, memory remaining, temperature, pressure, sensor type (e.g., optical versus electrical for heart rate), activity type, sensor placement, usage patterns, physical activity of the user, body position of the sensor, etc. For example, heart rate monitors can be optical and in a watch or earbud form factors versus a chest strap to measure electrical signals. Electrical signals are more accurate overall for heart rate, however optical heart rate monitors work fine for regular movements like running, biking, walking, and sitting still. Electrical signals are currently superior for yoga, weightlifting, tennis, and other irregular movements. Heart rate monitors can be worn, for example, on the wrist, chest, or ears. Step counters may be placed in a pocket, worn on a wrist, worn on a shoe, or worn on a belt clip. Being able to take these conditions into account to make decisions regarding intelligently leads to much more accurate and efficient results.

Referring again to FIG. 1, in a particular example first smart device 14*a* includes a heart rate sensor, glucose sensor, and blood pressure sensor. Second smart device 14*b* includes a hydration sensor, a step sensor, and a heart rate sensor. Third smart device 14*c* includes a temperature sensor, step sensor, and heart rate sensor. Accordingly, first smart device 14*a*, second smart device 14*b*, and third smart device 14*c* all include hear rate sensors such that a situation exists in which multiple smart devices collect the same type of sensor data. In some situations, it may not be desirable to collect heart rate data from all three sensors. In accordance with at least one embodiment, primary communication device 12 takes into account certain reliability factors related to each of the sensors including reliability, accuracy, reporting periodicity, and the operating conditions, to process the sensor data such as forming a weighted value for a given reporting time period, interpolating for a time period in which data is unavailable or a sensor is inoperative, or eliminating data from a particularly unreliable sensor. In one or more embodiments, primary communication device 12 determines a reliability factor for each sensor, determines whether data from one or more of the sensors is not to be used for processing by primary communication device 12 based upon the reliability factors, and may instruct one or more of first smart device 14*a*, second smart device 14*b*, and third smart device 14*c* to cease sending of sensor data of a specific sensor or power down a specific sensor if data from the particular sensor is not to be used for processing by primary communication device 12. As conditions surrounding smart devices 14*a*-14*c* change, so can the accuracy of the reporting as well. Thus, the ability to provide a dynamic sensor data reporting plan that is aimed at collecting an efficient and accurate sensor data given a dynamic sensor environment.

In one or more embodiments, a user context of a user associated with primary communication device 12 may be used as a reliability factor in determining whether data from a particular sensor of a particular smart device will be used for processing by primary communication device 12. For example, suppose a user has two smart devices, one a utilitarian, rubberized fitness smart device suitable for a user context in which the user is exercising, and another smart device that is jewelry for a user context in a more formal setting. During an exercise activity the user may not wish to wear the jewelry smart device, primary communication device 12 may take the user context into account by disregarding the sensor data from the fitness smart device. In particular embodiments, primary communication device 12 may have its own built-in sensor device as well and the user context may be used to determine whether data from these sensors will be used. For example, suppose a user places her primary communication device 12, e.g., smartphone) in a cup holder of a treadmill. Both second smart device 14*b* and primary communication device 12 may collect step data, and normally, the primary communication device 12 may be trusted for its step data more. However, when the phone is placed in the cup holder, it no longer becomes the dominant reporter of step information. Instead, primary communication device 12 switches to second smart device 14*b* for step information which has become more accurate. In some embodiments, the system makes a greedy decision by selecting the sensor with the largest reported value during a time period. In the cupholder example, primary communication device 12 may report zero steps while the secondary communication device may report a large number of steps. In some embodiments, a sudden change in the readings from a sensor may trigger a re-evaluation of which device is to be used. In the treadmill example, the sudden change in steps reported from primary communication device 12 may trigger a re-evaluation of whether to activate or start tracking the steps reported by the secondary smart device. In another embodiment, the system may look for consensus and take an average of the value coming from several sensors. In another embodiment, the system may take a hybrid approach by eliminating outlier data such as the highest or lowest value and averaging consensus across the other sensors. In some embodiments, the approach could vary by sensor type. For example, steps might be greedy, heart rate might be average, and speed might be hybrid.

In one or more embodiments, a data aggregation period associated with each of first smart device 14*a*, second smart device 14*b*, and third smart device 14*c* may be used as a reliability factor in determining whether sensor data from a particular sensor of a particular smart device will be used for processing by primary communication device 12. In some embodiments, different smart devices may have different aggregation periods. For example, one smart device might gather five minutes of step data before reporting the data to primary communication device, and another smart device may report data every 30 seconds. In accordance with at least one embodiment, such granularity can be taken into account when determining a sensor data reporting plan for a given a set of sensors and circumstances for a smart device.

In one or more embodiments, the accuracy of a sensor of a smart device may be used as a reliability factor in determining whether sensor data from a particular sensor of a particular smart device will be used for processing by primary communication device 12. In some examples, different sensors that report a same characteristic may have different accuracy. For example a first sensor of a first smart device may have a error of X % and a second sensor of a second smart device may have an error of Y % for the same characteristic. So, if one smart device's sensor inaccuracy becomes too great, its data can be thrown away. Alternatively, the less accurate data can be given a lower weight. In at least one embodiment, accuracy of a particular sensor may be unknown, and so baseline information about the user from another smart device known to be reasonably reliable can be used as an initial baseline/reference point. In some embodiments, sensors report accuracy information indicative of the accuracy of the sensor along with their sensor data to primary communication device 12. In other embodiments, the accuracy is known a priori to the primary communication device. For example, a manufacturer of primary communication device 12 can test many different sensors in a lab and determine approximate error. This pre-determined error can be provided to primary communication device 12 as a lookup table. For example, although GPS and a BLE foot pod may both report speed, GPS may be considered a priori to be less accurate than a BLE foot pod.

In one or more embodiments, the battery power level of a smart device may be used as a reliability factor in determining whether sensor data from a particular sensor of a particular smart device will be used for processing by primary communication device 12. In low battery power situations, a clock of a smart device may become less reliable, causing the sensor data collection and reporting also to become less reliable. In one embodiment, primary communication device 12 recognizes that the clock is inaccurate, and switches data collection from a sensor of the smart device having a low battery life to another sensor device of another smart device with a better battery life. As a result, more reliable values for the present condition are obtained. When the clock on the original smart device improves due to the battery level being restored, primary communication device 12 may switch back to the sensor of the previous smart device. In some embodiments, based on experience with how reporting of sensor values degrades with a degraded clock, primary communication device 12 may correct the reported values to offset the low power situation.

In other embodiments, the connection reliability of a smart device to primary communication device 12 may be used as a reliability factor in determining whether sensor data from the particular smart device will be reported to primary communication device 12. For example, a connection over Bluetooth low energy (BLE) uses the industrial, scientific, and medical radio band (ISM) band of the radio frequency (RF) spectrum. An advantage of BLE is that devices may freely transit in this band, but a disadvantage is it can become congested and interfered with by other communications in the spectrum. Since other RF bands ban interfere with BLE, this can be taken into account when developing a dynamic sensor data reporting plan. In this regard, depending on which smart devices are experiencing connection difficulty over BLE, this can be taken into account as part of the reliability calculus. For example, a sensor could be accurate to 0.0000000001 units, but if the value cannot be reported due to connection unreliability, then it is of no use, and a more reliable connection to a less accurate sensor can be employed.

In one or more embodiments, primary communication device 12 is configured to dynamically determine the set of sensors among smart devices that should be used across overlapping sensors based on reliability factors such as user context and history, accuracy of sensor data, and reliability of values of the sensor data. In still other embodiments, this information may be determined by network device 16, determined in a network cloud, or as a distributed effort by any or all of the devices in communication network 10 including one or more of primary communication device 12, first smart device 14a, second smart device 14b, third smart device 14c, and network device 16 that are configured to contribute to the overall sensor data reporting plan determination. For example, any of first smart device 14a, second smart device 14b, and third smart device 14c may designate one or more of smart devices 14a-14c to aggregate some or all of the reported data.

In one embodiment, a challenge/response mechanism is initially used between primary communication device 12 and each off first smart device 14a, second smart device 14b, and third smart device 14c to determine the capabilities of the particular smart device. Upon receiving the capabilities of each of smart devices 14a-14c, primary communication device 12 may determine whether it has historical information about the particular smart device, thereby receiving and analyzing information in response to querying as to which device is most appropriate for reporting a particular sensed parameter at the present time. In one or more embodiments, if no response is received from a particular smart device within a predetermined time period, the particular smart device can be considered to be or have become unavailable and thus no longer used for reporting. In another particular embodiment, if three smart devices are all reporting sensor data about the same parameter and the sensor data from one of the smart devices is out of range with the sensor data of the two other smart devices, the out of range data may be thrown away or ignored.

In still other embodiments, primary communication device 12 determines which smart device has a more accurate sensor of a similar sensor type based on a priori knowledge of earlier sensor data. For example, if a user is determined to be engaged in a running activity and has a heart rate of 70 beats per minute, but normally has a heart rate of 100 beats per minute when running, the heart rate value may be assumed to be incorrect. Thus, as a proxy for accuracy, a range can be determined within which data is determined to be acceptable. For example, a heart rate between 100 beats per minute and 190 beats per minute may be determined to be acceptable during a running activity. Heart rate data obtained from a sensor that is not within the range of 100-190 beats per minute may be discarded when the user is determined to be engaged in a running activity. In some embodiments, this range may change after a brief warmup period. In another embodiment, the acceptable range may vary based on data from another sensor. For example, the speed at which a user is running could be used to correlate with expected heart rate. In another example, power output could be used to correlated with expected heart rate. In a particular embodiment, user identity is data obtained from a network cloud and used as such a priori knowledge. In other particular embodiments, the acceptability of data is based on instantaneous information. Generally there is a range of values that are known to be acceptable or near acceptable. If sensor data is outside of this range, primary communication device 12 may consider rejecting the values, particularly if after consulting with another sensor of another smart device, the value is confirmed to be different from the 'normal' value reported by the other smart device. In certain examples, types of a priori knowledge associated with the user about what is expected as normal for the user may be based upon physiology, e.g., user height, user weight, history of heart rate ranges in past workouts, etc. In addition, dietary and medical history may be considered as certain foods, medical conditions and medical treatments may affect physiological responses. For example, the system may know that the user is taking a beta blocker which could lower heart rate. Alternatively, the system may know that the user is taking a stimulant such as caffeine which could increase heart rate.

In some embodiments, some smart devices may be smarter and/or have more sensors than other smart devices. In a particular embodiment, smart glasses as an intermediate sensor device can be used to aggregate sensor data from other smart devices, and then report the aggregate sensor data upon request by primary communication device 12. For example, the smart glasses themselves may have sensors including a barometer, step counter, GPS sensor, speed, stride rate, stride length, but may not have a power monitor or heart rate monitor. Accordingly, so parameters may not be able to be holistically determined by the smart glasses itself. In particular embodiments, the smart glasses may communicate with other wearable smart devices using a protocol, such as ANT or BLE, to instruct the other smart devices to report sensor data to the smart glasses for aggregation and batching at the smart glasses, and then sending the aggregate sensor data to primary communication device 12 upon request by primary communication device 12.

Figure 2:
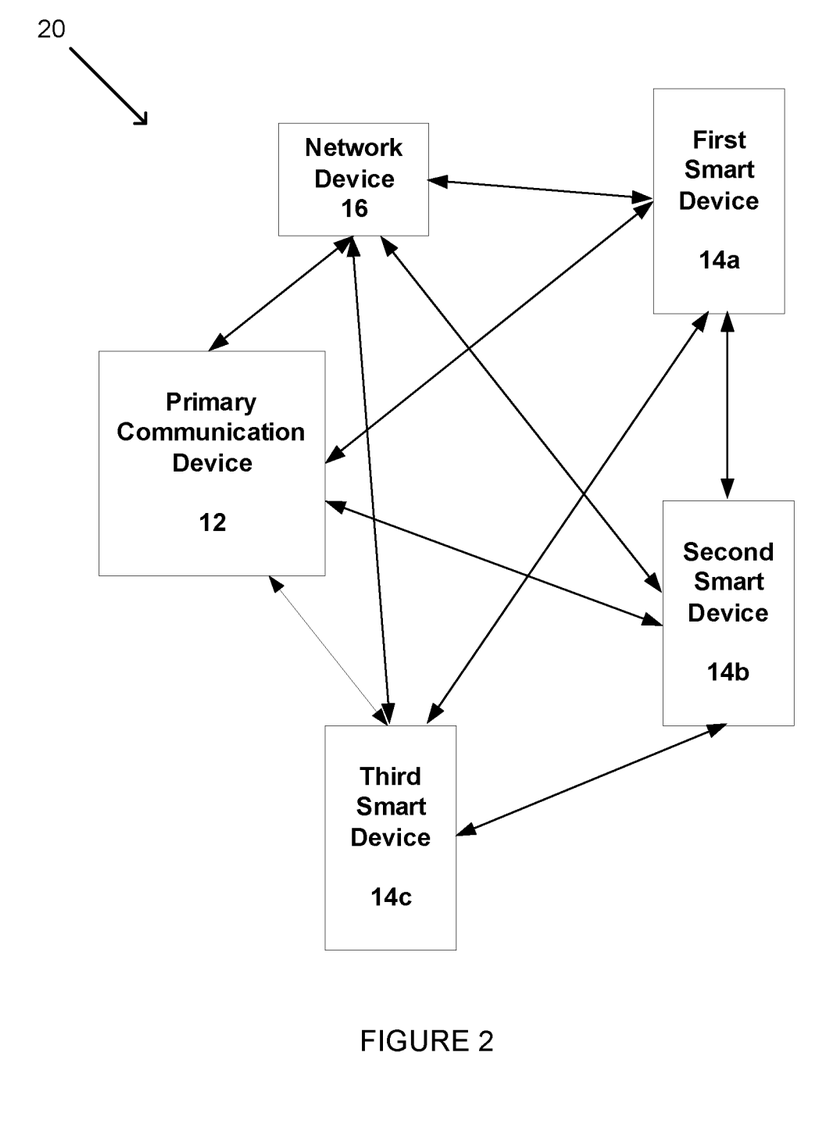
FIG. 2 illustrates another embodiment of a communication system for sensor data management for multiple smart devices.

FIG. 2 illustrates another embodiment of a communication system 20 for sensor data management for multiple smart devices. In the particular embodiment illustrated in FIG. 2, communication system 20 includes primary communication device 12, first smart device 14a, second smart device 14b, third smart device 14c, and network device 16. Primary communication device 12 is configured to wirelessly communicate with each of first smart device 14a, second smart device 14b, and third smart device 14c to receive data measured or otherwise obtained by one or more sensors of each of the respective smart devices 14a-14c. In addition, each of first smart device 14a, second device 14b, and third smart device 14c are configured to communicate sensor data among one another so that a particular one of first smart device 14a, second smart device 14b, and third smart device 14c is selected as a "master reporting device" device for a particular measured parameter. The "master reporting device" receives sensor data related to a particular parameter from one or more of the other smart devices, aggregates the sensor data from the multiple sensors, and performs any pre-processing on the data, e.g., weighting of the data from the different sensors. In certain embodiments, the "master reporting device" may send the aggregated data to primary communication device 12. In the embodiment of FIG. 2, network device 16 may also be configured to communicate with first smart device 14a, second device 14b, and third smart device 14c. In certain embodiments, either the "master reporting device" or primary communication device 12 may be configured to determine whether data from one or more of the sensors associated with a particular smart device is not to be used for processing by either primary communication device 12 or the "master reporting device" based upon one or more reliability factors, and may instruct one or more of first smart device 14a, second smart device 14b, and third smart device 14c to disable sending of sensor data of a specific sensor or power down a specific sensor if data from the particular sensor is not to be used for processing.

In one example first smart device 14a is designated as a "master step device" for aggregation and any pre-processing (e.g., weighting) of step data received from other smart devices such as third smart device 14c as well as its own obtained step data. Second smart device 14b is designated for aggregation of heart rate data received from first smart device 14a and third smart device 14c as well as its own heart rate data, and any pre-processing (e.g., weighting) of heart rate data as a "master heart rate data device." As conditions change, such as if a battery of first smart device 14a dies, a new master step device can be designated or primary communication device 12 can take control if no other suitable master step device exists. In a particular embodiment, a particular smart device, such as first smart device 14a may anticipate that due to a temperature exceeding 115 degrees Fahrenheit, its reporting will likely be faulty. In such a case, first smart device 14a may prohibit itself from participating in a sensor data reporting plan. In one or more embodiments, the determination of which smart devices will report sensor data and which sensors will be used can be dynamically determined based on a variety of reliability factors, and any of the connected devices, such as smart devices 14a-14c, network device 16, or primary communication device 12, can participate in an aggregation and/or pre-processing process to report the most relevant/accurate sensor data for a given context, and according to efficient scheduling/queuing/prioritization.

Figure 3:
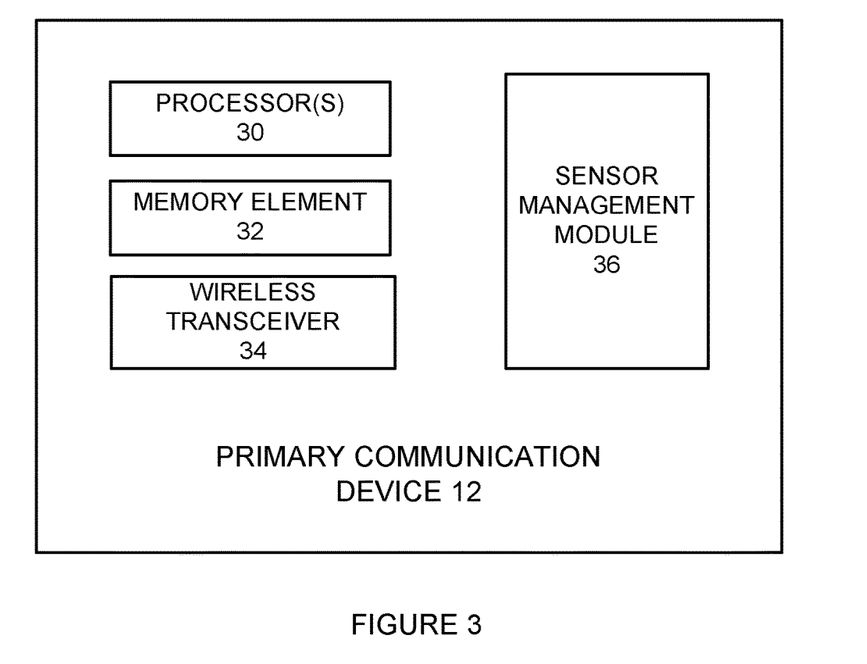
FIG. 3 illustrates an embodiment of primary communication device of the communication system of FIG. 1.

FIG. 3 illustrates an embodiment of primary communication device 12 of the communication system 10 of FIG. 1. In the particular embodiment illustrated in FIG. 3, primary communication device 12 includes one or more processor(s) 30, a memory element 32, a wireless transceiver 34, and a sensor management module 36. Processor(s) 30 is configured to execute software instructions to perform various operations of primary communication device 12 as described herein. Processor(s) 30 may be any type of processor, such as a micro-processor, an embedded processor, a digital signal processor (DSP), a network processor, or other device to execute code. Although only one processor(s) 30 is illustrated in FIG. 3, it should be understood that primary communication device 12 may include more than one processor in some embodiments. Memory element 32 may be configured to store software instructions and data associated with primary communication device 12 as well as sensor data obtained from one or more smart devices. Memory element 32 may be any suitable memory element (e.g., random access memory (RAM), read-only memory (ROM), erasable programmable ROM (EPROM), electrically erasable programmable ROM (EEPROM), application specific integrated circuit (ASIC), etc.), software, hardware, firmware, or in any other suitable component, device, element, or object where appropriate and based on particular needs. Any of the memory items discussed herein should be construed as being encompassed within the broad term 'memory element.' Moreover, the information being used, tracked, sent, or received in communication system 10 could be provided in any database, register, queue, table, cache, control list, or other storage structure, all of which can be referenced at any suitable timeframe. Any such storage options may also be included within the broad term 'memory element' as used herein.

Wireless transceiver 34 is configured to enable wireless communication with one or more of first smart device 14a, second smart device 14b, third smart device 14c and network device 16. In particular embodiments, wireless transceiver 34 may include one or more of a Bluetooth transceiver, a Wi-Fi transceiver, a 3G and/or 4G transceiver, an NFC transceiver, or any other suitable wireless transceiver. In one or more embodiments, wireless transceiver 34 is configured to receive sensor data from one or more of first smart device 14a, second smart device 14b, third smart device 14c. In one or more embodiments, wireless transceiver 34 may be further configured to transmit instructions to one or more of first smart device 14a, second smart device 14b, third smart device 14c instructing the particular smart device to not report data from a particular sensor if primary communication device 12 determines that the particular sensor will not be used during data collection. Sensor management module 36 includes software and/or hardware to facilitate management of sensor data for multiple smart devices as described herein. In an alternative embodiment, wireless transceiver 34 may be replaced by a non-wireless transceiver for use with a non-wireless networks of sensors such as smart clothing that contains several sensors functioning as a personal body network.

Figure 4:
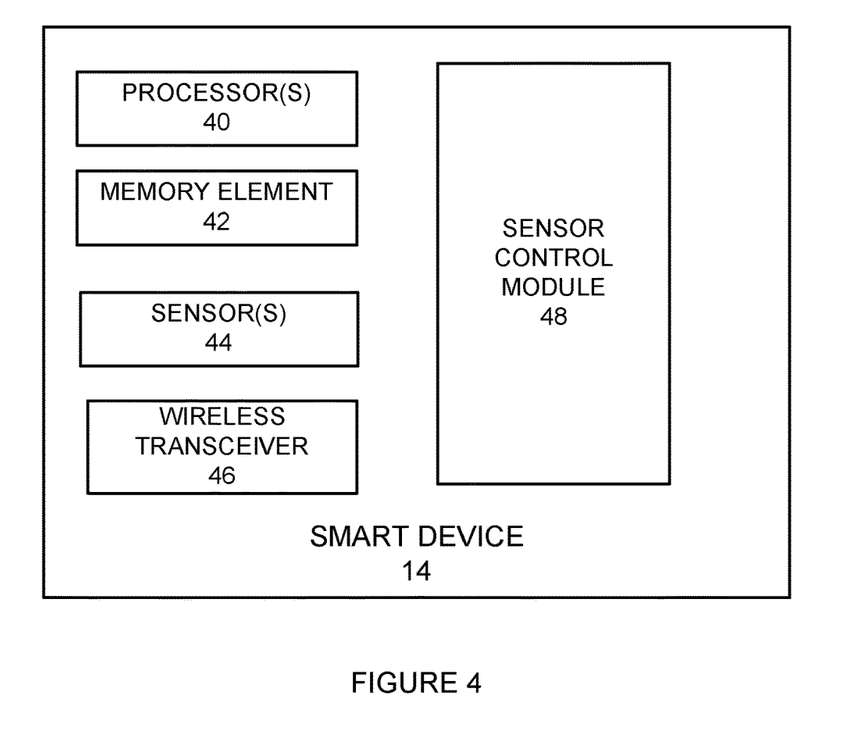
FIG. 4 illustrates an embodiment of a smart device of the communication system of FIG. 1.

FIG. 4 illustrates an embodiment of a smart device 14 of the communication system 10 of FIG. 1. In one or more embodiments, smart device 14 may include one or more of smart devices 14a-14c shown in FIG. 1. In the particular embodiment illustrated in FIG. 4, smart device 14 includes one or more processor(s) 40, a memory element 42, one or more sensors (44) a wireless transceiver 46, and sensor control module 48. Processor(s) 40 is configured to execute software instructions to perform various operations of smart device 14 as described herein. Processor(s) 40 may be any type of processor, such as a micro-processor, an embedded processor, a digital signal processor (DSP), a network processor, or other device to execute code. Although only one processor(s) 40 is illustrated in FIG. 4, it should be understood that smart device 14 may include more than one processor in some embodiments. Memory element 42 may be configured to store software instructions and data associated with smart device 12. Memory element 42 may be any suitable memory element (e.g., random access memory (RAM), read-only memory (ROM), erasable programmable ROM (EPROM), electrically erasable programmable ROM (EEPROM), application specific integrated circuit (ASIC), etc.), software, hardware, firmware, or in any other suitable component, device, element, or object where appropriate and based on particular needs. Any of the memory items discussed herein should be construed as being encompassed within the broad term 'memory element.' Moreover, the information being used, tracked, sent, or received in communication system 10 could be provided in any database, register, queue, table, cache, control list, or other storage structure, all of which can be referenced at any suitable timeframe. Any such storage options may also be included within the broad term 'memory element' as used herein.

Sensor(s) 44 may include any sensor configured to sense/measure a parameter associated with smart device 14 such as heart rate data, blood pressure data, step data, temperature data, glucose data, etc. Wireless transceiver 46 is configured to enable wireless communication with primary communication device 12, other smart devices and/or network element 16. In particular embodiments, wireless transceiver 46 may include one or more of a Bluetooth transceiver, a WiFi transceiver, a 3G and/or 4G transceiver, an NFC transceiver, or any other suitable wireless transceiver. In one or more embodiments, wireless transceiver 46 is configured to transmit sensor data to primary communication device 12 and/or other smart devices.

Sensor control module 48 includes software and/or hardware to facilitate control of sensor(s) 44 by smart device 14 as described herein. In one or more embodiments, sensor control module 48 is configured to receive an instruction from primary communication device 12 indicating that a particular sensor(s) 44 has been selected to not report its sensor data to primary communication device 12 as further described herein.

Figure 5:
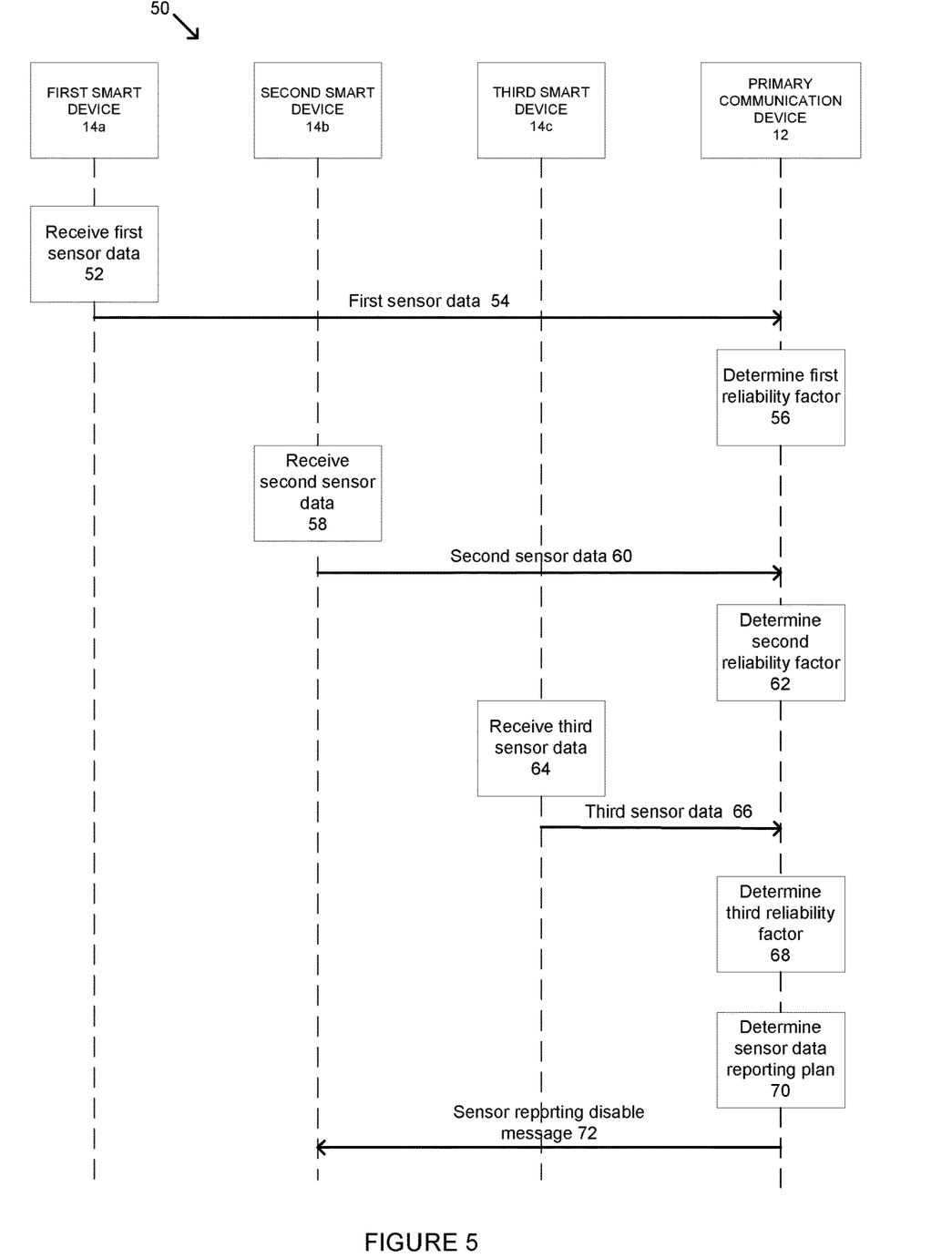
FIG. 5 illustrates a simplified flow diagram showing flows associated with the communication system of FIG. 1 in accordance with one embodiment.

FIG. 5 illustrates a simplified flow diagram 50 showing flows associated with the communication system of FIG. 1 in accordance with one embodiment. In 52, first smart device 14a receives first sensor data associated with a first sensor of first smart device 14a. In 54, first smart device 14a transmits the first sensor data to primary communication device 12. In 56, primary communication device 12 determines a first reliability factor associated with the first sensor data. In 58, second sensor device 14b receives second sensor data from a second sensor of second smart device 14b. In 60, second smart device 14b transmits the second sensor data to primary communication device 12. In 62, primary communication device 12 determines a second reliability factor associated with the second sensor data. In 64, third smart device 14c receives third sensor data from a third sensor of third smart device 14c. In 66, third smart device 14c transmits the third sensor data to primary communication device 12. In 68, primary communication device 12 determines a third reliability factor associated with the third sensor data.

In 70, primary communication device 12 determines a sensor data reporting plan based upon the first reliability factor, second reliability factor, and third reliability factor. The sensor data reporting plan indicates whether each of the first sensor, second sensor, and third sensor are to subsequently send their respective sensor data to primary communication device 12. In the particular embodiment illustrated in FIG. 5, primary communication device 12 determines that second sensor of second smart device 14b should not send the second sensor data to primary communication device 12. In 72, primary communication device 12 sends a sensor reporting disable message to second smart device 14b indicating that reporting of the second sensor data associated with the second sensor of second smart device 14b is to be disabled. Although the embodiment of FIG. 5 is illustrated using three smart devices in communication system 10, it should be understood that in other embodiments any number of smart devices may be present.

Figure 6:
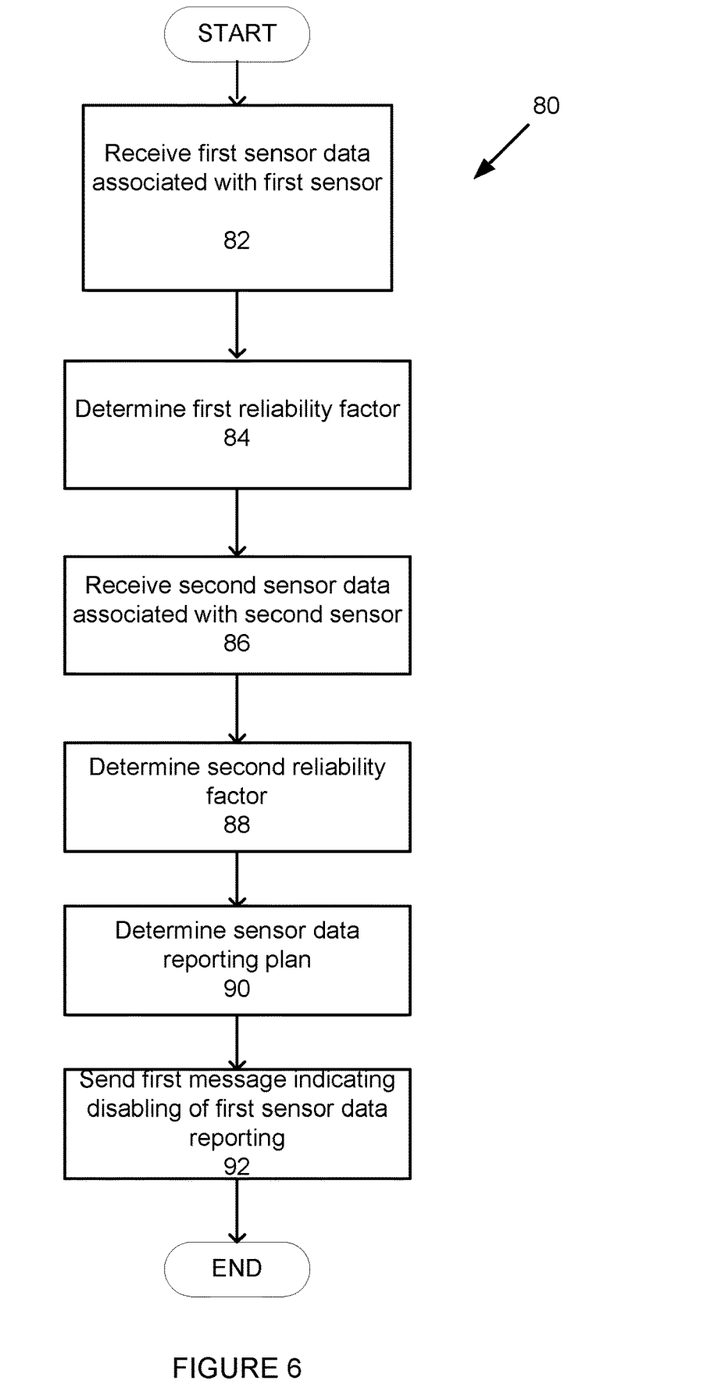
FIG. 6 illustrates a simplified flow chart showing operations associated with the primary communication device of FIG. 1.

FIG. 6 illustrates a simplified flow chart 80 showing operations associated with primary communication device 12 of FIG. 1. In 82, primary communication device 12 receives first sensor data associated with a first sensor of a first smart device. In 84, primary communication device 12 determines a first reliability factor associated with the first sensor data. In 86, primary communication device 12 receives second sensor data associated with a second sensor of a second smart device. In 88, primary communication device 12 determines a second reliability factor associated with the second sensor data. In 90, a sensor data reporting plan is determined based upon the first reliability factor and the second reliability factor. The sensor data reporting plan indicates whether each of the first sensor and the second sensor are to subsequently send their respective sensor data to primary communication device 12.

In 92, responsive to determining that the first sensor is not to subsequently send the first sensor data to the primary communication device, primary communication device 12 sends a first message to the first smart device indicating that reporting of the first sensor data associated with the first sensor of first smart device is to be disabled. The operations then end.

In particular embodiments, the first smart device is configured to disable reporting of the first sensor data to the primary communication device responsive to receiving the first message. In other embodiments, the primary communication device receives accuracy information from the first smart device indicative of the accuracy of the first sensor and/or receives accuracy information from the second smart device indicative of the accuracy of the second sensor.

In other particular embodiments, one of the first smart device and a second smart device are designated as a master reporting device, wherein the master reporting device is configured to aggregate the first sensor data and the second sensor data as aggregate sensor data. In other particular embodiments, the master reporting device is further configured to send the aggregate sensor data to the primary communication device. In a particular embodiment, the determining of the sensor data reporting plan is performed by the primary communication device.

In at least one embodiment, the first reliability factor includes at least one of a context of a user associated with the primary communication device, an accuracy of the first sensor, a reporting periodicity of the first smart device, operating conditions of the first smart device, a battery power level of the first smart device, and a connection reliability between the first smart device and the primary communication device. In a particular embodiment, at least one of the first sensor data and the second sensor data includes biometric data. In another particular embodiment, the primary communication device includes a smartphone. In still another particular embodiment, at least one of the first smart device and the second smart device includes a wearable device.

In regards to the internal structure associated with communication system 10, each of primary communication device 12, first smart device 14a, second smart device 14b, third smart device 14c, and network device 16 can include memory elements for storing information to be used in the operations outlined herein. Each of primary communication device 12, first smart device 14a, second smart device 14b, third smart device 14c, and network device 16 may keep information in any suitable memory element (e.g., random access memory (RAM), read-only memory (ROM), erasable programmable ROM (EPROM), electrically erasable programmable ROM (EEPROM), application specific integrated circuit (ASIC), etc.), software, hardware, firmware, or in any other suitable component, device, element, or object where appropriate and based on particular needs. Any of the memory items discussed herein should be construed as being encompassed within the broad term 'memory element.' Moreover, the information being used, tracked, sent, or received in communication system 10 could be provided in any database, register, queue, table, cache, control list, or other storage structure, all of which can be referenced at any suitable timeframe. Any such storage options may also be included within the broad term 'memory element' as used herein.

In certain example implementations, the functions outlined herein may be implemented by logic encoded in one or more tangible media (e.g., embedded logic provided in an ASIC, digital signal processor (DSP) instructions, software (potentially inclusive of object code and source code) to be executed by a processor, or other similar machine, etc.), which may be inclusive of non-transitory computer-readable media. In some of these instances, memory elements can store data used for the operations described herein. This includes the memory elements being able to store software, logic, code, or processor instructions that are executed to carry out the activities described herein.

In an example implementation, network elements of communication system 10, such as primary communication device 12, first smart device 14a, second smart device 14b, third smart device 14c, and network device 16, may include software modules to achieve, or to foster, operations as outlined herein. These modules may be suitably combined in any appropriate manner, which may be based on particular configuration and/or provisioning needs. In certain embodiments, such operations may be carried out by hardware, implemented externally to these elements, or included in some other network device to achieve the intended functionality. Furthermore, the modules can be implemented as software, hardware, firmware, or any suitable combination thereof. These elements may also include software (or reciprocating software) that can coordinate with other network elements in order to achieve the operations, as outlined herein.

Additionally, each of primary communication device 12, first smart device 14a, second smart device 14b, third smart device 14c, and network device 16 may include a processor that can execute software or an algorithm to perform activities as discussed herein. A processor can execute any type of instructions associated with the data to achieve the operations detailed herein. In one example, the processors could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an EPROM, an EEPROM) or an ASIC that includes digital logic, software, code, electronic instructions, or any suitable combination thereof. Any of the potential processing elements, modules, and machines described herein should be construed as being encompassed within the broad term 'processor.'

EXAMPLES

The following examples pertain to further embodiments.

Example 1 is an apparatus, comprising logic, at least partially incorporated into hardware, to: receive first sensor data associated with a first sensor of a first smart device; determine a first reliability factor associated with the first sensor data; receive second sensor data associated with a second sensor of a second smart device; determine a second reliability factor associated with the second sensor data; and determine a sensor data reporting plan based upon the first reliability factor and the second reliability factor, the sensor data reporting plan indicating whether each of the first sensor and the second sensor are to subsequently send their respective sensor data to a primary communication device.

In Example 2, the subject matter of Example 1 can optionally include wherein the logic is further to: responsive to determining that the first sensor is not to subsequently send the first sensor data to the primary communication device, send a first message to the first smart device indicating that reporting of the first sensor data associated with the first sensor of first smart device is to be disabled.

In Example 3, the subject matter of Example 2 can optionally include wherein the first smart device is configured to disable reporting of the first sensor data to the primary communication device responsive to receiving the first message.

In Example 4, the subject matter of Example 1 can optionally include wherein the logic is further to: receive accuracy information from the first smart device indicative of the accuracy of the first sensor.

In Example 5, the subject matter of Example 1 can optionally include wherein the logic is further to: designate one of the first smart device and a second smart device as a master reporting device, wherein the master reporting device is configured to aggregate the first sensor data and the second sensor data as aggregate sensor data.

In Example 6, the subject matter of Example 5 can optionally include wherein the master reporting device is further configured to send the aggregate sensor data to the primary communication device.

In Example 7, the subject matter of Example 1 can optionally include wherein the determining of the sensor data reporting plan is performed by the primary communication device.

In Example 8, the subject matter of Example 1 can optionally include wherein the first reliability factor includes at least one of a context of a user associated with the primary communication device, an accuracy of the first sensor, a reporting periodicity of the first smart device, operating conditions of the first smart device, a battery power level of the first smart device, a sensory type, physical activity of the user, body position of the sensor, and a connection reliability between the first smart device and the primary communication device.

In Example 9, the subject matter of Example 1 can optionally include wherein at least one of the first sensor data and the second sensor data includes biometric data.

In Example 10, the subject matter of Example 1 can optionally include wherein the primary communication device includes one of a smartphone, a tablet computer, a laptop computer, a desktop computer, and a smart watch.

In Example 11, the subject matter of Example 1 can optionally include wherein at least one of the first smart device and the second smart device includes a wearable device.

Example 12 is at least one non-transitory computer storage medium to store computer code comprising: computer code to receive first sensor data associated with a first sensor of a first smart device; computer code to determine a first reliability factor associated with the first sensor data; computer code to receive second sensor data associated with a second sensor of a second smart device; computer code to determine a second reliability factor associated with the second sensor data; and computer code to determine a sensor data reporting plan based upon the first reliability factor and the second reliability factor, the sensor data reporting plan indicating whether each of the first sensor and the second sensor are to subsequently send their respective sensor data to a primary communication device.

In Example 13, the subject matter of Example 12 can optionally include computer code to responsive to determining that the first sensor is not to subsequently send the first sensor data to the primary communication device, send a first message to the first smart device indicating that reporting of the first sensor data associated with the first sensor of first smart device is to be disabled.

In Example 14, the subject matter of Example 13 can optionally include wherein the first smart device is configured to disable reporting of the first sensor data to the primary communication device responsive to receiving the first message.

In Example 15, the subject matter of Example 12 can optionally include computer code to designate one of the first smart device and a second smart device as a master reporting device, wherein the master reporting device is configured to aggregate the first sensor data and the second sensor data as aggregate sensor data.

In Example 16, the subject matter of Example 15 can optionally include wherein the master reporting device is further configured to send the aggregate sensor data to the primary communication device.

In Example 17, the subject matter of Example 1 can optionally include wherein the determining of the sensor data reporting plan is performed by the primary communication device.

Example 18 is a computer-implemented method comprising: receiving first sensor data associated with a first sensor of a first smart device; determining a first reliability factor associated with the first sensor data; receiving second sensor data associated with a second sensor of a second smart device; determining a second reliability factor associated with the second sensor data; and determining a sensor data reporting plan based upon the first reliability factor and the second reliability factor, the sensor data reporting plan indicating whether each of the first sensor and the second sensor are to subsequently send their respective sensor data to a primary communication device.

In Example 19, the subject matter of Example 18 can optionally include responsive to determining that the first sensor is not to subsequently send the first sensor data to the primary communication device, send a first message to the first smart device indicating that reporting of the first sensor data associated with the first sensor of first smart device is to be disabled.

In Example 20, the subject matter of Example 19 can optionally include wherein the first smart device is configured to disable reporting of the first sensor data to the primary communication device responsive to receiving the first message.

In Example 21, the subject matter of Example 18 can optionally include designating one of the first smart device and a second smart device as a master reporting device, wherein the master reporting device is configured to aggregate the first sensor data and the second sensor data as aggregate sensor data.

In Example 22, the subject matter of Example 21 can optionally include wherein the master reporting device is further configured to send the aggregate sensor data to the primary communication device.

Example 23 is an apparatus comprising: means for receiving first sensor data associated with a first sensor of a first smart device; means for determining a first reliability factor associated with the first sensor data; means for receiving second sensor data associated with a second sensor of a second smart device; means for determining a second reliability factor associated with the second sensor data; and means for determining a sensor data reporting plan based upon the first reliability factor and the second reliability factor, the sensor data reporting plan indicating whether each of the first sensor and the second sensor are to subsequently send their respective sensor data to a primary communication device.

In Example 24, the subject matter of Example 23 can optionally include means for responsive to determining that the first sensor is not to subsequently send the first sensor data to the primary communication device, sending a first message to the first smart device indicating that reporting of the first sensor data associated with the first sensor of first smart device is to be disabled.

In Example 25, the subject matter of Example 24 can optionally include wherein the first smart device is configured to disable reporting of the first sensor data to the primary communication device responsive to receiving the first message.

In Example 26, the subject matter of Examples 23-24 can optionally include means for designating one of the first smart device and a second smart device as a master reporting device, wherein the master reporting device is configured to aggregate the first sensor data and the second sensor data as aggregate sensor data.

In Example 27, the subject matter of Example 26 can optionally include wherein the master reporting device is further configured to send the aggregate sensor data to the primary communication device.

In Example 28, the subject matter of Examples 23-24 can optionally include wherein the determining of the sensor data reporting plan is performed by the primary communication device.

Example 29 is an apparatus, comprising logic, at least partially incorporated into hardware, to: receive first sensor data associated with a first sensor of a first smart device; determine a first reliability factor associated with the first sensor data; receive second sensor data associated with a second sensor of a second smart device; determine a second reliability factor associated with the second sensor data; and determine a sensor data reporting plan based upon the first reliability factor and the second reliability factor, the sensor data reporting plan indicating whether each of the first sensor and the second sensor are to subsequently send their respective sensor data to a primary communication device.

In Example 30, the subject matter of Example 29 can optionally include responsive to determining that the first sensor is not to subsequently send the first sensor data to the primary communication device, send a first message to the first smart device indicating that reporting of the first sensor data associated with the first sensor of first smart device is to be disabled.

In Example 31, the subject matter of Example 30 can optionally include wherein the first smart device is configured to disable reporting of the first sensor data to the primary communication device responsive to receiving the first message.

In Example 32, the subject matter of Examples 29-30 can optionally include wherein the logic is further to: receive accuracy information from the first smart device indicative of the accuracy of the first sensor.

In Example 33, the subject matter of Examples 29-30 can optionally include wherein the logic is further to: designate one of the first smart device and a second smart device as a master reporting device, wherein the master reporting device is configured to aggregate the first sensor data and the second sensor data as aggregate sensor data.

In Example 34, the subject matter of Example 33 can optionally include wherein the master reporting device is further configured to send the aggregate sensor data to the primary communication device.

In Example 35, the subject matter of Examples 29-30 can optionally include wherein the determining of the sensor data reporting plan is performed by the primary communication device.

In Example 36, the subject matter of Examples 29-30 can optionally include wherein the first reliability factor includes at least one of a context of a user associated with the primary communication device, an accuracy of the first sensor, a reporting periodicity of the first smart device, operating conditions of the first smart device, a battery power level of the first smart device, a sensory type, physical activity of the user, body position of the sensor, and a connection reliability between the first smart device and the primary communication device.

In Example 37, the subject matter of Examples 29-30 can optionally include wherein at least one of the first sensor data and the second sensor data includes biometric data.

In Example 38, the subject matter of Examples 29-30 can optionally include wherein the primary communication device includes one of a smartphone, a tablet computer, a laptop computer, a desktop computer, and a smart watch.

In Example 39, the subject matter of Examples 29-30 can optionally include wherein at least one of the first smart device and the second smart device includes a wearable device.

Example 40 is at least one non-transitory computer storage medium to store computer code comprising: computer code to receive first sensor data associated with a first sensor of a first smart device; computer code to determine a first reliability factor associated with the first sensor data; computer code to receive second sensor data associated with a second sensor of a second smart device; computer code to determine a second reliability factor associated with the second sensor data; and computer code to determine a sensor data reporting plan based upon the first reliability factor and the second reliability factor, the sensor data reporting plan indicating whether each of the first sensor and the second sensor are to subsequently send their respective sensor data to a primary communication device.

In Example 40, the subject matter of Example 41 can optionally include computer code to responsive to determining that the first sensor is not to subsequently send the first sensor data to the primary communication device, send a first message to the first smart device indicating that reporting of the first sensor data associated with the first sensor of first smart device is to be disabled.

In Example 42, the subject matter of Example 41 can optionally include wherein the first smart device is configured to disable reporting of the first sensor data to the primary communication device responsive to receiving the first message.

In Example 43, the subject matter of Examples 40-41 can optionally include computer code to designate one of the first smart device and a second smart device as a master reporting device, wherein the master reporting device is configured to aggregate the first sensor data and the second sensor data as aggregate sensor data.

In Example 44, the subject matter of Example 43 can optionally include wherein the master reporting device is further configured to send the aggregate sensor data to the primary communication device.

In Example 45, the subject matter of Examples 40-41 can optionally include wherein the determining of the sensor data reporting plan is performed by the primary communication device.

Example 46 is a computer-implemented method comprising: receiving first sensor data associated with a first sensor of a first smart device; determining a first reliability factor associated with the first sensor data; receiving second sensor data associated with a second sensor of a second smart device; determining a second reliability factor associated with the second sensor data; and determining a sensor data reporting plan based upon the first reliability factor and the second reliability factor, the sensor data reporting plan indicating whether each of the first sensor and the second sensor are to subsequently send their respective sensor data to a primary communication device.

In Example 47, the subject matter of Example 46 can optionally include responsive to determining that the first sensor is not to subsequently send the first sensor data to the primary communication device, send a first message to the first smart device indicating that reporting of the first sensor data associated with the first sensor of first smart device is to be disabled.

In Example 48, the subject matter of Example 47 can optionally include wherein the first smart device is configured to disable reporting of the first sensor data to the primary communication device responsive to receiving the first message.

In Example 49, the subject matter of Examples 46-47 can optionally include designating one of the first smart device and a second smart device as a master reporting device, wherein the master reporting device is configured to aggregate the first sensor data and the second sensor data as aggregate sensor data.

In Example 50, the subject matter of Example 49 can optionally include wherein the master reporting device is further configured to send the aggregate sensor data to the primary communication device.

Example 51 is a method comprising: receiving first sensor data associated with a first sensor of a first smart device; determining a first reliability factor associated with the first sensor data; receiving second sensor data associated with a second sensor of a second smart device; determining a second reliability factor associated with the second sensor data; and determining a sensor data reporting plan based upon the first reliability factor and the second reliability factor, the sensor data reporting plan indicating whether each of the first sensor and the second sensor are to subsequently send their respective sensor data to a primary communication device.

In Example 52, the subject matter of Example 51 can optionally include responsive to determining that the first sensor is not to subsequently send the first sensor data to the primary communication device, sending a first message to the first smart device indicating that reporting of the first sensor data associated with the first sensor of first smart device is to be disabled.

In Example 53, the subject matter of Example 52 can optionally include wherein the first smart device is configured to disable reporting of the first sensor data to the primary communication device responsive to receiving the first message.

In Example 54, the subject matter of Examples 51-52 can optionally include receiving accuracy information from the first smart device indicative of the accuracy of the first sensor.

In Example 55, the subject matter of Examples 51-52 can optionally include designating one of the first smart device and a second smart device as a master reporting device, wherein the master reporting device is configured to aggregate the first sensor data and the second sensor data as aggregate sensor data.

In Example 56, the subject matter of Example 55 can optionally include wherein the master reporting device is further configured to send the aggregate sensor data to the primary communication device.

In Example 57, the subject matter of Examples 51-52 can optionally include wherein the determining of the sensor data reporting plan is performed by the primary communication device.

In Example 58, the subject matter of Examples 51-52 can optionally include wherein the first reliability factor includes at least one of a context of a user associated with the primary communication device, an accuracy of the first sensor, a reporting periodicity of the first smart device, operating conditions of the first smart device, a battery power level of the first smart device, a sensory type, physical activity of the user, body position of the sensor, and a connection reliability between the first smart device and the primary communication device.

In Example 59, the subject matter of any Examples 51-52 can optionally include wherein at least one of the first sensor data and the second sensor data includes biometric data.

In Example 60, the subject matter of Examples 51-52 can optionally include wherein the primary communication device includes one of a smartphone, a tablet computer, a laptop computer, a desktop computer, and a smart watch.

Example 61 is an apparatus comprising means for performing the method of any of the preceding claims.

In Example 62, the subject matter of Example 61 can optionally include wherein the means for performing the method comprise a processor and a memory.

In Example 63, the subject matter of Example 62 can optionally include wherein the memory comprises machine-readable instructions, that when executed cause the apparatus to perform the method of any of Examples 51-60.

In Example 64, the subject matter of Examples 61-63 can optionally include wherein the apparatus is a computing system.

Example 65 is at least one computer readable medium comprising instructions that, when executed, implement a method or realize an apparatus as found in any preceding Example.

What is claimed is:

1. A primary communication device comprising:
    an antenna configured to receive one or more sensor data;
    non-volatile memory;
    a battery; and
    a processor with logic configured to:
        receive first sensor data associated with a first sensor of a first smart device;
        determine a first reliability factor associated with the first sensor data;
        receive second sensor data associated with a second sensor of a second smart device;
        determine a second reliability factor associated with the second sensor data; and
        determine a sensor data reporting plan based upon the first reliability factor and the second reliability factor, the sensor data reporting plan indicating whether at least one of the first sensor and the second sensor are to subsequently send their respective sensor data to the processor of the primary communication device;
    wherein, the first and second reliability factors are indicators of accuracy of the first and second sensor data, respectively.

2. The communication device of claim 1, wherein the logic is further to: responsive to determining that the first sensor is not to subsequently send the first sensor data to the primary communication device, sending a first message to the first smart device indicating that reporting of the first sensor data associated with the first sensor of the first smart device is to be disabled.

3. The primary communication device of claim 2, wherein the first smart device is configured to disable reporting of the first sensor data to the primary communication device responsive to receiving the first message.

4. The primary communication device of claim 1, wherein the logic is further to:
receive accuracy information from the first smart device indicative of the accuracy of the first sensor.

5. The primary communication device of claim 1, wherein the logic is further to:
designate one of the first smart device and the second smart device as a master reporting device, wherein the master reporting device is configured to aggregate the first sensor data and the second sensor data as aggregate sensor data.

6. The primary communication device of claim 5, wherein the master reporting device is further configured to send the aggregate sensor data to the primary communication device.

7. The primary communication device of claim 1, wherein the determining of the sensor data reporting plan is performed by the primary communication device.

8. The primary communication device of claim 1, wherein the first reliability factor includes at least one of a context of a user associated with the primary communication device, an accuracy of the first sensor, a reporting periodicity of the first smart device, operating conditions of the first smart device, a battery power level of the first smart device, a sensory type, physical activity of the user, body position of the first sensor, and a connection reliability between the first smart device and the primary communication device.

9. The primary communication device of claim 1, wherein at least one of the first sensor data and the second sensor data includes biometric data.

10. The primary communication device of claim 1, wherein the primary communication device includes one of a smartphone, a tablet computer, a laptop computer, a desktop computer, and a smart watch.

11. The primary communication device of claim 1, wherein at least one of the first smart device and the second smart device includes a wearable device.

12. A primary communication device comprising:
an antenna configured to receive sensor data;
a battery;
non-volatile memory including instruction configured with:
computer code to receive first sensor data associated with a first sensor of a first smart device;
computer code to determine a first reliability factor associated with the first sensor data;
computer code to receive second sensor data associated with a second sensor of a second smart device;
computer code to determine a second reliability factor associated with the second sensor data; and
computer code to determine a sensor data reporting plan based upon the first reliability factor and the second reliability factor, the sensor data reporting plan indicating whether at least of the first sensor and the second sensor are to subsequently send their respective sensor data to the primary communication device;
wherein, the first and second reliability factors are indicators of accuracy of the first and second sensor data, respectively.

13. The primary communication device of claim 12, further comprising: computer code to be responsive to determining that the first sensor is not to subsequently send the first sensor data to the primary communication device, sending a first message to the first smart device indicating that reporting of the first sensor data associated with the first sensor of the first smart device is to he disabled.

14. The primary communication device of claim 13, wherein the first smart device is configured to disable reporting of the first sensor data to the primary communication device responsive to receiving the first message.

15. The primary communication device of claim 12, further comprising computer code to designate one of the first smart device and the second smart device as a master reporting device, wherein the master reporting device is configured to aggregate the first sensor data and the second sensor data as aggregate sensor data.

16. The primary communication device of claim 15, wherein the master reporting device is further configured to send the aggregate sensor data to the primary communication device.

17. The primary communication device of claim 12, wherein the determining of the sensor data reporting plan is performed by the primary communication device.

18. An apparatus comprising:
means for receiving first sensor data associated with a first sensor of a first smart device;
means for determining a first reliability factor associated with the first sensor data;
means for receiving second sensor data associated with a second sensor of a second smart device;
means for determining a second reliability factor associated with the second sensor data; and
means for determining a sensor data reporting plan based upon the first reliability factor and the second reliability factor, the sensor data reporting plan indicating whether at least one of the first sensor and the second sensor are to subsequently send their respective sensor data to a primary communication device;
wherein, the first and second reliability factors are indicators of accuracy of the first and second sensor data respectively.

19. The apparatus of claim 18, further comprising responsive to determining that the first sensor is not to subsequently send the first sensor data to the primary communication device, sending a first message to the first smart device indicating that reporting of the first sensor data, associated with the first sensor of the first smart, device is to be disabled.

20. The apparatus of claim 19, wherein the first smart device is configured to disable reporting of the first sensor data to the primary communication device responsive to receiving the first message.

21. The apparatus of claim 18, further comprising designating one of the first smart device and the second smart device as a master reporting device, wherein the master reporting device is configured to aggregate the first sensor data and the second sensor data as aggregate sensor data.

22. The apparatus of claim 21, wherein the master reporting device is further configured to send the aggregate sensor data to the primary communication device.

* * * * *

UNITED STATES PATENT AND TRADEMARK OFFICE
CERTIFICATE OF CORRECTION

PATENT NO. : 11,317,832 B2
APPLICATION NO. : 15/089411
DATED : May 3, 2022
INVENTOR(S) : Daniel Jepson et al.

It is certified that error appears in the above-identified patent and that said Letters Patent is hereby corrected as shown below:

In the Claims

In Column 19, Claim 10, Line 42, delete "sniartphone," and insert -- smartphone, --, therefor.

In Column 20, Claim 13, Line 10, delete "to he" and insert -- to be --, therefor.

In Column 20, Claim 18, Line 43, delete "sensor data" and insert -- sensor data, --, therefor.

In Column 20, Claim 19, Line 49, delete "sensor data," and insert -- sensor data --, therefor.

In Column 20, Claim 19, Line 49, delete "smart, device" and insert -- smart device --, therefor.

Signed and Sealed this
Fifth Day of July, 2022

Katherine Kelly Vidal
*Director of the United States Patent and Trademark Office*